United States Patent
Hu

(10) Patent No.: US 10,273,802 B2
(45) Date of Patent: Apr. 30, 2019

(54) ATTRIBUTE-INDEXED MULTI-INSTRUMENT LOGGING OF DRILL CUTTINGS

(71) Applicant: HALLIBURTON ENERGY SERVICES, INC., Houston, TX (US)

(72) Inventor: Dandan Hu, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 15/519,818

(22) PCT Filed: Nov. 17, 2014

(86) PCT No.: PCT/US2014/065988
§ 371 (c)(1),
(2) Date: Apr. 17, 2017

(87) PCT Pub. No.: WO2016/080955
PCT Pub. Date: May 26, 2016

(65) Prior Publication Data
US 2017/0248016 A1    Aug. 31, 2017

(51) Int. Cl.
*E21B 49/00* (2006.01)
*E21B 49/08* (2006.01)
(Continued)

(52) U.S. Cl.
CPC ............ *E21B 49/08* (2013.01); *E21B 49/005* (2013.01); *G01N 23/046* (2013.01);
(Continued)

(58) Field of Classification Search
CPC .. E21B 49/08; E21B 2049/085; G01N 23/046
See application file for complete search history.

(56) References Cited

U.S. PATENT DOCUMENTS

| 6,220,371 | B1 | 4/2001 | Sharma et al. |
| 6,832,158 | B2 | 12/2004 | Mese et al. |

(Continued)

FOREIGN PATENT DOCUMENTS

| WO | 2013/058672 | 4/2013 |
| WO | 2014/025970 | 2/2014 |

OTHER PUBLICATIONS

PCT International Search Report and Written Opinion, dated Jul. 29, 2015, Appl No. PCT/US2014/065988, "Attribute-Indexed Multi-Instrument Logging of Drill Cuttings," Filed Nov. 17, 2014, 10 pgs.
(Continued)

*Primary Examiner* — Christine S. Kim
(74) *Attorney, Agent, or Firm* — Jason Sedano; Parker Justiss, P.C.

(57) ABSTRACT

A method according to some embodiments comprises obtaining a formation sample from a borehole, identifying minerals present in a first portion of the formation sample and determining densities of the minerals. The method also comprises determining, using a second portion of the formation sample, material properties associated with the mineral densities. The method further comprises associating the material properties with the identified minerals using the mineral densities, and generating a log comprising the associations.

16 Claims, 6 Drawing Sheets

(51) Int. Cl.
  *G01N 23/2252* (2018.01)
  *G01N 23/046* (2018.01)
(52) U.S. Cl.
  CPC .... *G01N 23/2252* (2013.01); *E21B 2049/085* (2013.01); *G01N 2223/405* (2013.01); *G01N 2223/616* (2013.01); *G01N 2223/633* (2013.01)

(56) References Cited

U.S. PATENT DOCUMENTS

| | | |
|---|---|---|
| 7,309,983 B2 | 12/2007 | Freedman |
| 8,191,416 B2 | 6/2012 | Kuchuk et al. |
| 8,217,337 B2 | 7/2012 | Neville et al. |
| 8,331,626 B2 | 12/2012 | Wojcik et al. |
| 8,550,184 B2 | 10/2013 | Buchanan |
| 8,590,382 B2 | 11/2013 | Zaleski et al. |
| 8,621,920 B2 | 1/2014 | Reid et al. |
| 8,725,477 B2 | 5/2014 | Zhang et al. |
| 2009/0103677 A1 | 4/2009 | Wood et al. |
| 2012/0221306 A1 | 8/2012 | Hurley et al. |
| 2012/0232859 A1 | 9/2012 | Pomerantz et al. |
| 2012/0277996 A1 | 11/2012 | Hurley et al. |
| 2012/0290208 A1 | 11/2012 | Jiang et al. |
| 2013/0018587 A1 | 1/2013 | Clark et al. |
| 2013/0073207 A1 | 3/2013 | Ganz |
| 2013/0124094 A1 | 5/2013 | Galford |
| 2013/0259190 A1* | 10/2013 | Walls ............ G01N 23/22 378/9 |
| 2013/0308753 A1 | 11/2013 | Groves et al. |
| 2013/0308759 A1 | 11/2013 | Pettinato |
| 2013/0308831 A1 | 11/2013 | Dvorkin et al. |
| 2017/0108483 A1* | 4/2017 | Clark ............ G01N 33/24 |
| 2018/0003786 A1* | 1/2018 | Washburn ......... G01R 33/4808 |

OTHER PUBLICATIONS

Cole, David R. et al., "Properties of CO2-Rich Pore Fluids", Geothermal Technologies Program 2010 Peer Review Presentation, May 20, 2010, p. 1-14., US Department of Energy, Oak Ridge National Laboratory, Oak Ridge, Tennessee, United States, Available at: http://energy.gov/eere/geothermal/downloads/properties-co2-rich-pore-fluids-and-their-effect-porosity-evolution-egs, May 20, 2010, 12 pgs.

Haberlah, David, "Integrated wellsite petrography solution proved by onshore test in Papua New Guinea", World Oil, Jan. 2012, p. 67-72, vol. 233, No. 1, Gulf Publishing Company, Houston, Texas, United States, Jan. 2012, 4 pgs.

Schlumberger, "Neoscope Sourceless Formation Evaluation While Drilling", NeoScope Brochure, 2012, p. 1-7, Schlumberger Limited, Houston, Texas, United States, Available at: http://www.slb.com/NeoScope.aspx, 2012, 12 pgs.

\* cited by examiner

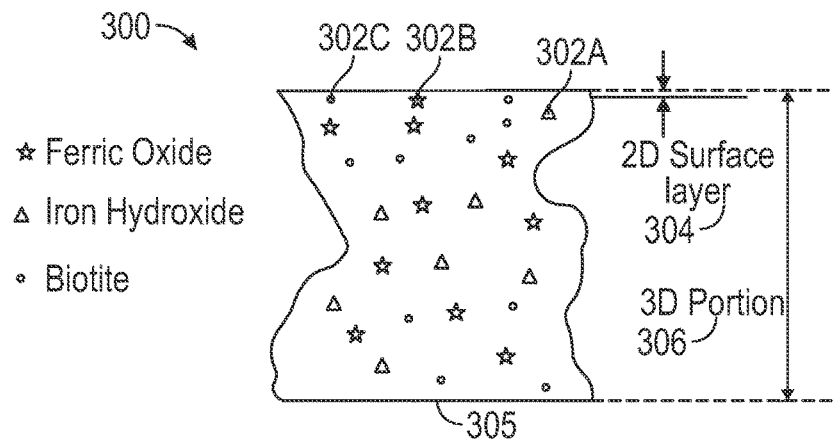
FIG. 3A
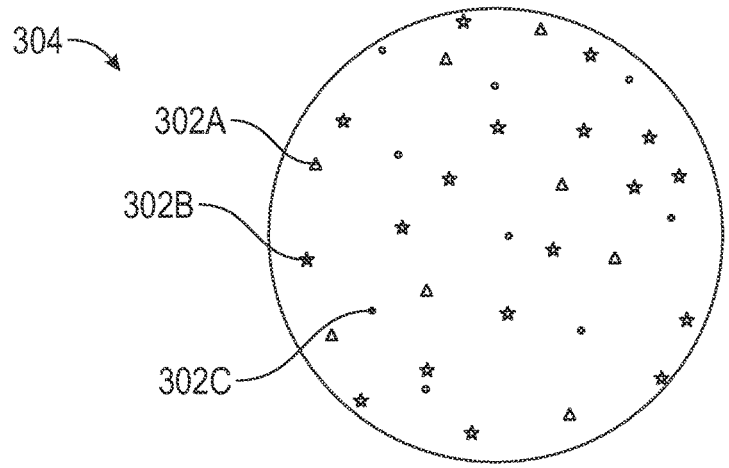
FIG. 3B
| EDS Results | |
|---|---|
| Mineral Identity | Density |
| Ferric Oxide | 5.24 g/cm$^3$ |
| Iron Hydroxide | 3.40 g/cm$^3$ |
| Biotite | 3.09 g/cm$^3$ |
FIG. 3C

| CT Results | | |
|---|---|---|
| Mineral Number | Material Properties | Density |
| 1 | X | 3.09 g/cm$^3$ |
| 2 | Y | 5.24 g/cm$^3$ |
| 3 | Z | 3.40 g/cm$^3$ |

322     324     326

307

| EDS Results-Ordered ||
|---|---|
| Mineral Identity | Density |
| Biotite | Ascending Order ↓ |
| Iron Hydroxide | |
| Ferric Oxide | |

| CT Results-Ordered |||
|---|---|---|
| Mineral Number | Material Properties | Density |
| 1 | X | Ascending Order ↓ |
| 3 | Z | |
| 2 | Y | |

| Mineral Identity | Material Properties |
|---|---|
| Biotite | X |
| Iron Hydroxide | Z |
| Ferric Oxide | Y |

ATTRIBUTE-INDEXED MULTI-INSTRUMENT LOGGING OF DRILL CUTTINGS

BACKGROUND

Learning the material properties of subsurface formations may be advantageous for a variety of reasons. For instance, such information may give clues as to rock permeability, the types and amounts of mineral deposits, and grain size distribution. This information is invaluable in estimating the amount and location of hydrocarbon reserves and in determining the most effective strategies for extracting such hydrocarbons. Among the various potential sources of such information are the drill cuttings from the formations of interest. As the drill bit removes fragments of material from the bottom of the borehole, the fragments are carried to the surface by a drilling fluid and screened from the flow stream. The screened material may be periodically sampled and subjected to laboratory analysis.

There are potential shortcomings to the available laboratory analysis techniques. Some instruments provide volumetric analysis with very limited resolution and types of measurement information, while other instruments provide extremely detailed information that is limited to a shallow surface analysis. There does not yet exist a tool that yields an extremely detailed volumetric analysis in a manner that is feasible for cuttings-based logging.

BRIEF DESCRIPTION OF THE DRAWINGS

Accordingly, there are disclosed in the accompanying drawings and in the following description methods and systems for accurately determining formation sample material properties in a detailed, volumetric fashion. The methods and systems entail analyzing the formation sample using multiple imaging techniques with at least one common attribute for indexing and correlating the results of the analyses, thereby improving accuracy in comparison to other methods and systems for determining material properties. In the drawings:

FIG. 3A is a cross-sectional view of a formation sample containing multiple minerals, in accordance with embodiments;

FIG. 3B is a top-down view of a surface layer of the formation sample of FIG. 3A, in accordance with embodiments;

FIG. 3C is a table containing results of an energy dispersive spectrometry (EDS) procedure performed on the formation sample surface layer of FIG. 3B, in accordance with embodiments;

FIG. 5A shows an EDS scanning results table ordered according to relative density values;

FIG. 5B shows a CT scanning results table ordered according to relative density values; and FIG. 6 is a table showing relationships determined using the tables of FIGS. 3C, 4C and/or 5A-5B.

Figure 1:
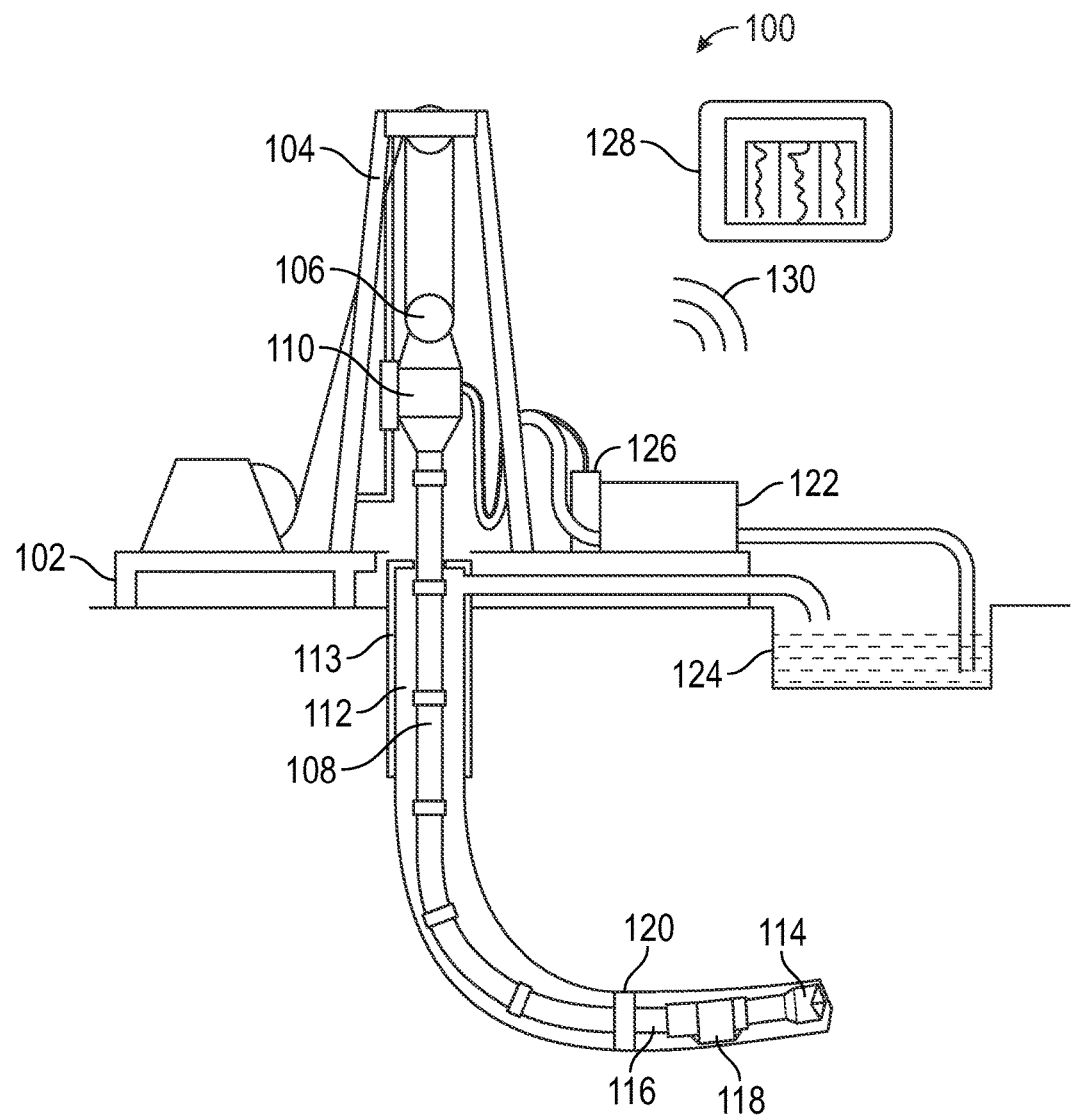
FIG. 1 is a schematic view of an illustrative drilling environment, in accordance with embodiments.

It should be understood that the specific embodiments given in the drawings and detailed description do not limit the disclosure. On the contrary, they provide the foundation for one of ordinary skill to discern the alternative forms, equivalents, and modifications that are encompassed together with one or more of the given embodiments in the scope of the appended claims. In addition, the term "or" as used in the description and claims shall be interpreted in an inclusive sense.

DETAILED DESCRIPTION

The difficulties outlined above are addressed at least in part by the disclosed methods and systems for accurately determining formation sample material properties. The methods and systems entail analyzing a formation sample using multiple imaging techniques and indexing and correlating the results of the analyses. More specifically, the disclosed methods and systems entail performing an energy dispersive spectrometry (EDS) procedure to identify the minerals present in a surface layer of a formation sample and to determine the densities associated with each of these minerals. The methods and systems also include performing a computerized tomography (CT) procedure, optionally using a formation sample container that enables the simultaneous CT imaging of multiple samples, to identify a number of different minerals present in the entire formation sample as well as the densities and other relevant material properties (e.g., count information) associated with each of those different minerals. The technique further entails ordering (i.e., indexing) data tables describing the results of the EDS and CT procedures, identifying relationships or associations using the ordered data tables, and generating a log comprising the relationships or associations.

FIG. 1 is a schematic view of an illustrative drilling environment 100 by which formation samples may be obtained. The drilling environment 100 comprises a drilling platform 102 that supports a derrick 104 having a traveling block 106 for raising and lowering a drill string 108. A top-drive motor 110 supports and turns the drill string 108 as it is lowered into a borehole 112. The drill string's rotation, alone or in combination with the operation of a downhole motor, drives the drill bit 114 to extend the borehole 112. The drill bit 114 is one component of a bottomhole assembly (BHA) 116 that may further include a rotary steering system (RSS) 118 and stabilizer 120 (or some other form of steering assembly) along with drill collars and logging instruments. A pump 122 circulates drilling fluid through a feed pipe to the top drive 110, downhole through the interior of drill string 108, through orifices in the drill bit 114, back to the surface via an annulus around the drill string 108, and into a retention pit 124. The drilling fluid transports formation samples—i.e., drill cuttings—from the borehole 112 into the retention pit 124 and aids in maintaining the integrity of the borehole. Formation samples may be extracted from the drilling fluid at any suitable time and location, such as from the retention pit 124. The formation samples may then be analyzed at a suitable surface-level laboratory or other facility (not specifically shown). While drilling, an upper portion of the borehole 112 may be stabilized with a casing string 113 while a lower portion of the borehole 112 remains open (uncased).

The drill collars in the BHA 116 are typically thick-walled steel pipe sections that provide weight and rigidity for the drilling process. The thick walls are also convenient sites for installing logging instruments that measure downhole conditions, various drilling parameters, and characteristics of the formations penetrated by the borehole. The BHA 116 typically further includes a navigation tool having instruments for measuring tool orientation (e.g., multi-component magnetometers and accelerometers) and a control sub with a telemetry transmitter and receiver. The control sub coordinates the operation of the various logging instruments, steering mechanisms, and drilling motors, in accordance with commands received from the surface, and provides a stream of telemetry data to the surface as needed to communicate relevant measurements and status information. A corresponding telemetry receiver and transmitter is located on or near the drilling platform 102 to complete the telemetry link. The most popular telemetry link is based on modulating the flow of drilling fluid to create pressure pulses that propagate along the drill string ("mud-pulse telemetry or MPT"), but other known telemetry techniques are suitable. Much of the data obtained by the control sub may be stored in memory for later retrieval, e.g., when the BHA 116 physically returns to the surface.

A surface interface 126 serves as a hub for communicating via the telemetry link and for communicating with the various sensors and control mechanisms on the platform 102. A data processing unit (shown in FIG. 1 as a tablet computer 128) communicates with the surface interface 126 via a wired or wireless link 130, collecting and processing measurement data to generate logs and other visual representations of the acquired data and the derived models to facilitate analysis by a user. The data processing unit may take many suitable forms, including one or more of: an embedded processor, a desktop computer, a laptop computer, a central processing facility, and a virtual computer in the cloud. In each case, software on a non-transitory information storage medium may configure the processing unit to carry out the desired processing, modeling, and display generation.

Figure 2:
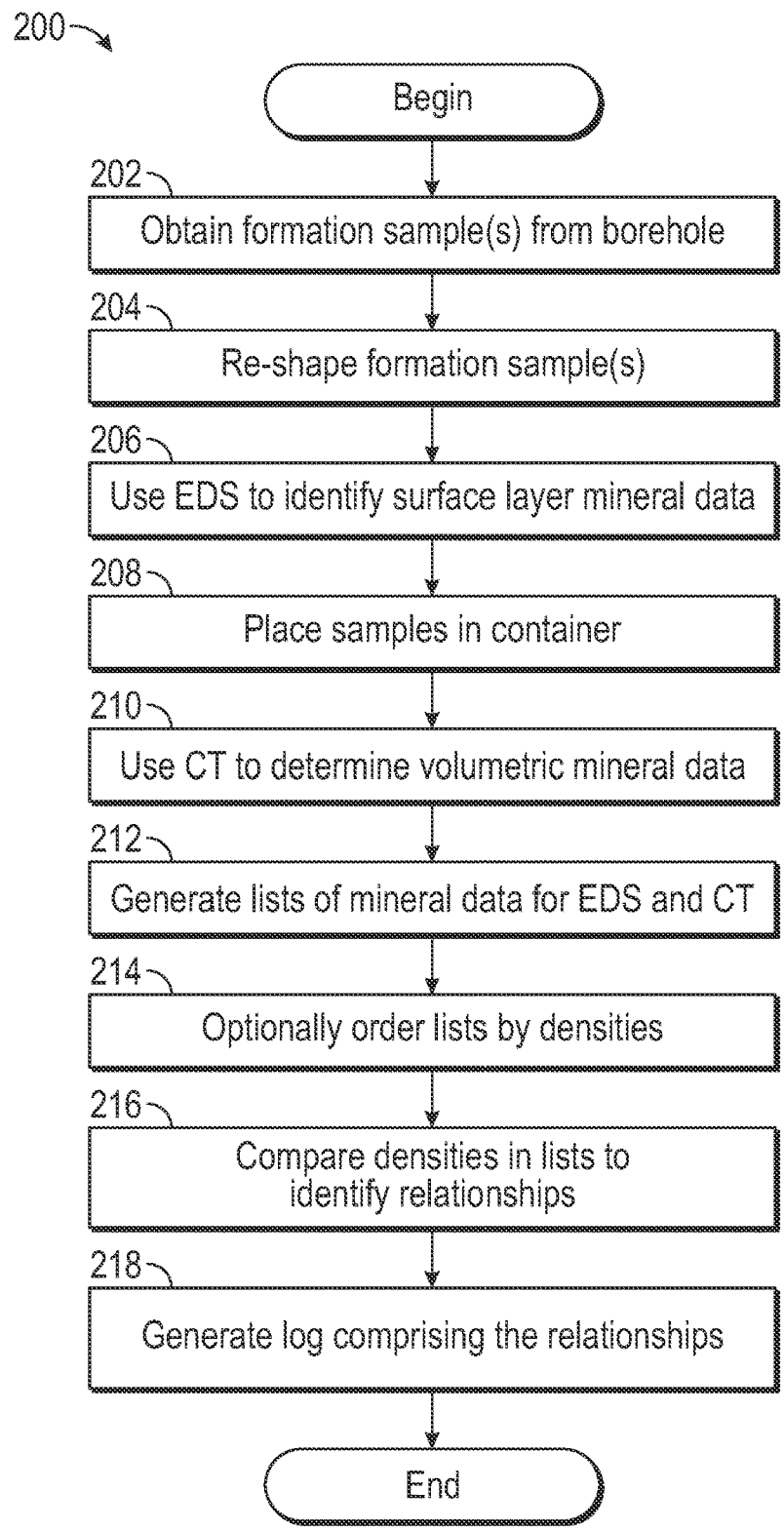
FIG. 2 is a flow diagram of a method implementing the formation sample analysis techniques described herein, in accordance with embodiments.

FIG. 2 is a flow diagram of a method 200 in accordance with embodiments, and the method 200 is described with reference to FIGS. 3A-6. Method 200 begins by obtaining one or more formation samples from a borehole (step 202). As explained above, formation samples typically are drill cuttings that are extracted from drilling fluid in the retention pit 126, although such drill cuttings may be obtained from the drilling fluid in any suitable manner. It may be useful to determine—using known techniques—the downhole location (e.g., depth) from which each particular drill cutting is obtained. Comparing the results of formation sample analysis with data regarding the subsurface locations from which those samples were obtained aids in drawing conclusions about the material properties of the subsurface formations at those locations.

When performing subsequent steps of method 200, it may be necessary to re-shape the formation samples so that they are more suitable for those steps. For instance, in some embodiments, when performing EDS and/or CT it is desirable to have formation samples that have substantially flat top and bottom surfaces. Thus, the formation samples obtained from the drilling fluid may be re-shaped to have flat or substantially flat top and bottom surfaces. Formation samples may be re-shaped, if necessary, using any of a variety of known techniques (step 204). One such known technique comprises the use of a mold. The formation sample and resin material are poured into the mold and then the mold is placed in a mixer. After the sample and resin are mixed, the mixture is removed from the mold and cross-sectioned to achieve flat top and/or bottom surfaces. The sample is then coated with a conductive surface, such as carbonate, chromium, or gold.

FIG. 3A shows an illustrative formation sample 300 that has been re-shaped in accordance with step 204 of method 200. Formation sample 300 comprises a top surface layer 304 and a bottom surface 305. Surface layer 304 may be of any suitable thickness but, in at least some embodiments, when it is analyzed using EDS as described below, only its two-dimensional surface is analyzed. In contrast, numeral 306 indicates a three-dimensional ("volumetric") portion of the formation sample 300 that is larger (e.g., thicker) than surface layer 304. In some embodiments, volumetric portion 306 comprises the entire formation sample 300. In other embodiments, the thickness of volumetric portion 306 is between that of the entire formation sample 300 and a thickness greater than that of the surface layer 304. Volumetric portion 306 of the formation sample 300 is analyzed using CT or any other suitable three-dimensional imaging technique, also described below.

Formation samples typically comprise one or more minerals. Illustrative formation sample 300 comprises three different minerals—ferric oxide, iron hydroxide and biotite, minerals commonly found in subsurface shale formations. FIG. 3A indicates these minerals with numerals 302A, 302B, and 302C, which refer to iron hydroxide, ferric oxide, and biotite, respectively. As shown, the minerals are found throughout the formation sample 300 in varying amounts and in varying locations. Each of the three minerals in the formation sample 300 constitutes a different percentage of the formation sample 300. These percentages are known as "count information," or simply as "counts." Mineral counts—along with other, similar information, such as grain size distribution—are material properties of the formation sample.

Surface layers of formation sample are analyzed using EDS, and volumetric portions of formation samples are analyzed using CT scanning. Individually, neither of these imaging technologies is adequate to identify both minerals present throughout the formation sample and the material properties of those minerals throughout the formation sample. This is because EDS—which is performed only on the surface layer of a formation sample—yields information about the minerals present in the formation layer and those minerals' densities. EDS may not, however, accurately identify material properties of those minerals throughout the formation sample 300. On the other hand, CT—which is performed on a volumetric portion of a formation sample—accurately identifies the number of different minerals present in the formation sample, the densities of those minerals, and material properties of those minerals throughout the formation sample 300. CT may not, however, accurately identify what these minerals actually are. Thus, each of these techniques—EDS and CT—may lack key information about the minerals present in the formation sample 300. EDS may not properly identify the minerals' material properties throughout the formation sample 300, while CT may not properly identify the minerals' identities. Both the techniques, however, may accurately identify the absolute densities of the minerals—or, at a minimum, they accurately identify the relative densities of the minerals. This common measure—density—can be used to correlate information obtained by EDS (mineral identities) with information obtained by CT (material properties) to identify which material properties correspond to which mineral identities. To achieve this commonality, in some embodiments, the imaging resolutions used when performing EDS and CT scanning techniques are identical or at least vary by no more than 1 μm. Similarly, in some embodiments, the formation sample is oriented the same way when performing EDS and CT. The resulting density information is accurate for the entire formation sample 300.

Accordingly, referring back to FIG. 2, the method 200 comprises using EDS to identify minerals present in the surface layer and each such mineral's density (step 206). FIG. 3B is a top-down view of this surface layer 304. As explained above, in embodiments, EDS is performed only on the surface layer 304, resulting in the information shown in table 307 of FIG. 3C (step 212). Specifically, table 307 comprises column 308, which lists mineral identities determined using EDS of the surface layer 304, and it also comprises column 309, which lists absolute densities determined using EDS of the surface layer 304. FIG. 3C shows illustrative mineral identities and densities—namely, ferric oxide, with a density of 5.24 g/cm$^3$, iron hydroxide, with a density of 3.40 g/cm$^3$, and biotite, with a density of 3.09 g/cm$^3$. (In some embodiments, absolute densities are not identified, so minerals are ordered by relative density—i.e., the minerals are listed in ascending or descending order by density. These embodiments are discussed below with respect to FIGS. 5A-5B.) As explained, these mineral identities and densities are typically valid for all of the formation sample 300. The table 307, however, does not include material properties of the surface layer 304, because such information would not be valid for the formation sample 300 as a whole.

Figure 4A:
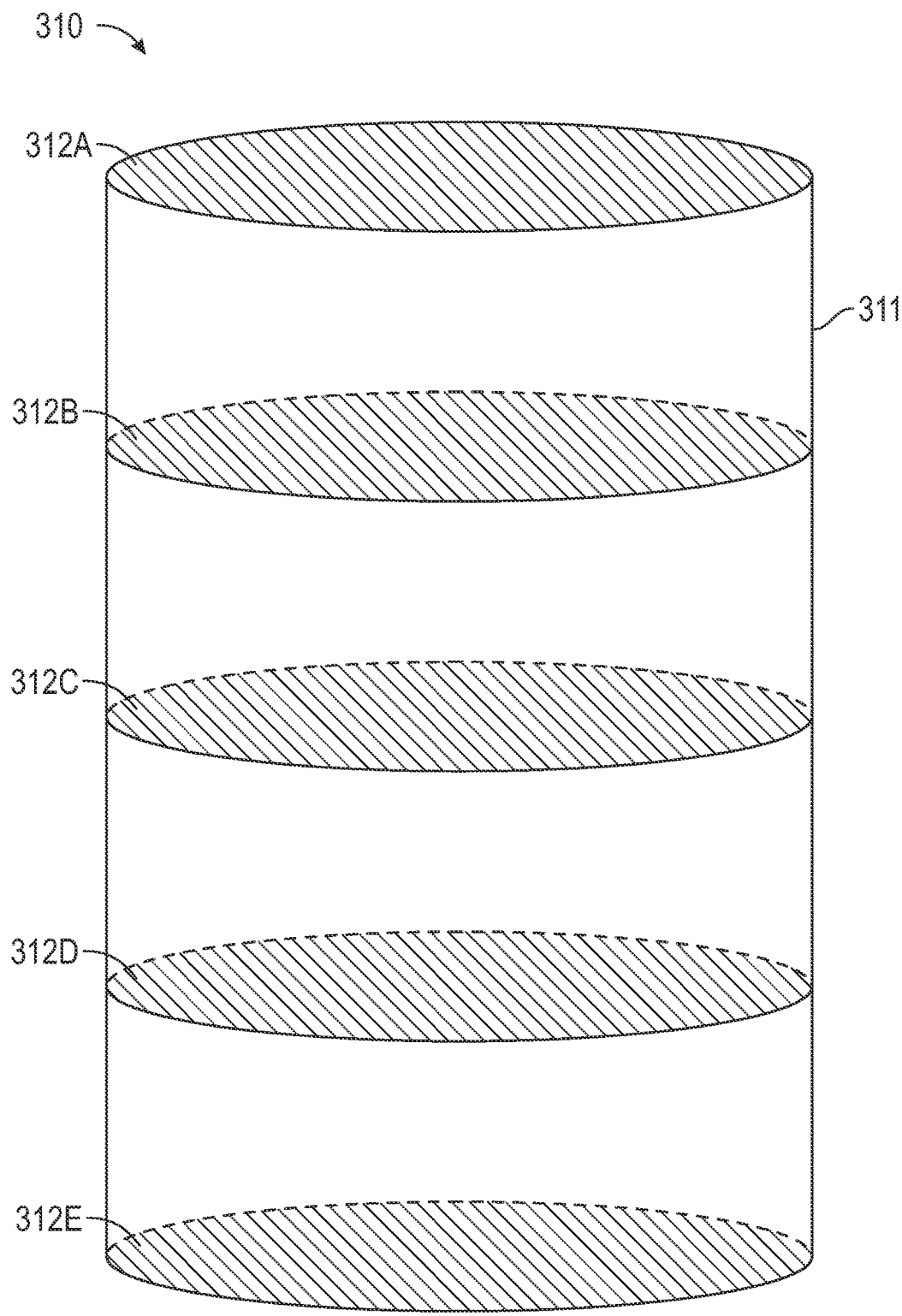
FIG. 4A is a perspective view of a formation sample container having multiple partitions, in accordance with embodiments.
Figures 4B, 4C:
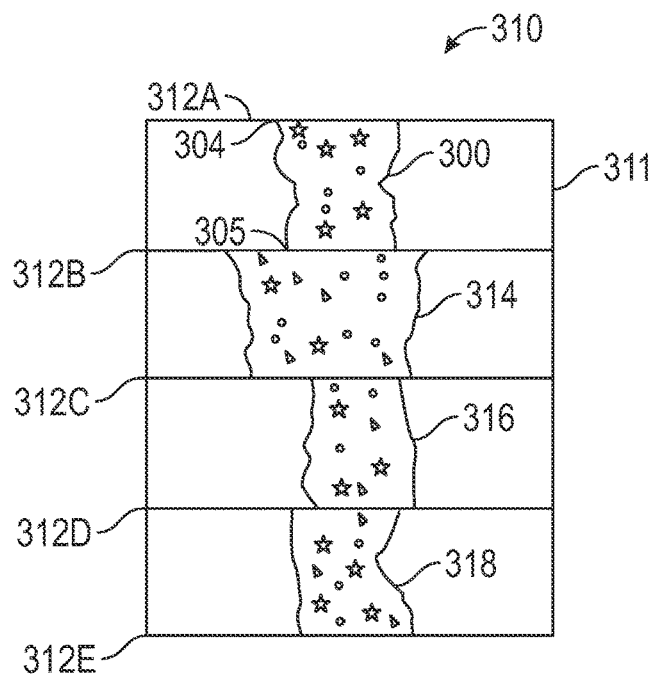
FIG. 4B is a cross-sectional view of the formation sample container of FIG. 4A containing multiple formation samples, in accordance with embodiments.
FIG. 4C is a table containing results of a computerized tomography (CT) procedure performed on the formation sample of FIG. 3A, in accordance with embodiments.

FIG. 4A shows a formation sample container assembly 310 comprising a cylindrical container 311 and multiple partitions 312A-312E. The cylindrical container 311 and/or the partitions 312A-312E preferably are made of a low-density material, such as plastic, although any suitable material may be used. The partitions 312A-312E preferably comprise a cylindrical shape, as shown. The container 311 is usable to hold one or more formation samples during the CT scanning process. As shown in FIGS. 2 and 4B, formation samples 300, 314, 316 and 318 are placed between partitions 312A-312E and, in particular, they are disposed within the container 311 such that the top surface of each formation sample contacts one partition and the bottom surface of each formation sample contacts another partition (step 208). For instance, formation sample 300 is held in place by pressure that partition 312A exerts on the surface layer 304 and by support that partition 312B provides to the bottom surface 305. In this way, the partitions hold the formation samples in place. In at least some embodiments, the partitions are sufficiently heavy that they remain immobilized during a typical CT scanning procedure, although other immobilization mechanisms, such as clips and notches, also are contemplated and fall within the scope of this disclosure.

The formation samples in the assembly 310 shown in FIG. 4B are subsequently analyzed using CT scanning technology (step 210). The resulting three-dimensional CT images are analyzed using any suitable technique, such as the image segmentation technique. Table 320 of FIG. 4C shows illustrative results of the CT scanning procedure (step 212). In particular, table 320 comprises column 322, which lists an arbitrarily assigned mineral number for temporary identification purposes since CT scanning cannot determine mineral identities; column 324, which lists material properties associated with each detected mineral; and column 326, which lists the density associated with each such mineral. As with EDS results table 307, table 320 may list absolute density values or, in some embodiments, the data may simply be listed in ascending or descending order by relative density. In addition, although CT results table 320 lists generic material property placeholders X, Y and Z, in practice, a CT results table 320 lists material properties such as count information and grain size distribution. In at least some embodiments, relative densities are determined by evaluating the relative intensities of the minerals in the CT images. Further, in at least some embodiments, count information—that is, an accurate representation of the percentage of the formation sample that each mineral constitutes—is determined from the CT images by image segmentation processing. More specifically, the CT images are divided into clusters based on differences in intensity, and the percentage of the total sample that each intensity cluster constitutes is then determined.

The tables in FIGS. 3C and 4C have one field in common—absolute density (or, in some embodiments, relative density). Thus, density may be used to correlate the remaining information in table 307—namely, mineral identities—with the remaining information in table 320—namely, material properties. If absolute density values are used in tables 307 and 320, step 214 of method 200—in which the tables are optionally ordered by density—is unnecessary, and control of the method 200 proceeds to step 216.

In step 216, the method 200 comprises comparing the density values in the two tables to correlate mineral identities with mineral material properties, as shown in table 600 of FIG. 6. Table 600 comprises column 602, which lists mineral identities, and column 604, which lists material properties (e.g., count information) of those identities. Referring simultaneously to FIGS. 3C, 4C and 6, the mineral biotite has a density of 3.09 g/cm$^3$ (table 307) and a density of 3.09 g/cm$^3$ corresponds to material property "X" (table 320). Thus, biotite must have material property "X" (table 600). Similarly, iron hydroxide has a density of 3.40 g/cm$^3$ (table 307), which corresponds to material property "Z" (table 320). Thus, iron hydroxide must have material property "Z" (table 600). Likewise, ferric oxide has a density of 5.24 g/cm$^3$ (table 307), corresponding to material property "Y" (table 320). Thus, ferric oxide must have material property "Y" (table 600). The relationships shown in FIG. 6 are representative of the entire formation sample 300. Method 200 finally comprises generating a log comprising the relationships (step 218).

For embodiments in which absolute density values are not obtained in tables 307 and 320, or in which density values for a common mineral in the two tables may not match exactly, the method 200 comprises performing step 214. For these embodiments, in step 214, the tables 307 and 320 are ordered by relative density. Preferably, both tables 307 and 320 are indexed in ascending order by relative density, or they are both indexed in descending order by relative density. FIG. 5A shows an ordered version of table 307, in which the minerals are ordered by ascending relative density. Similarly, FIG. 5B shows an ordered version of table 320, in which the minerals and their respective material properties (e.g., count information) are ordered by ascending relative density. In this way, even though absolute density values may not be available, the minerals' relative density values—i.e., the knowledge that a particular density value, while not precisely known, is greater than, less than, or equal to another known or unknown density value—are sufficient to determine which mineral identity corresponds to which material property.

This technique of using relative densities to correlate information between the tables is made possible at least in part by the fact that both EDS and CT are able to detect all minerals present in the formation sample 300. Thus, because all minerals are accounted for in both tables, and because all entries in the tables are listed by ascending or descending relative density, the above-described correlations are possible. In these embodiments, the method 200 comprises comparing the ordered tables to identify the relationships shown in table 600 of FIG. 6 (step 216). Logs comprising the relationships are subsequently generated (step 218).

Numerous other variations and modifications will become apparent to those skilled in the art once the above disclosure is fully appreciated. For example, the steps shown in method 200 are merely illustrative, and various additions, deletions and other modifications may be made as desired and appropriate. It is intended that the following claims be interpreted to embrace all such variations, modifications and equivalents.

The present disclosure encompasses numerous embodiments. At least some of these embodiments are directed to a method that comprises obtaining a formation sample from a borehole; identifying minerals present in a first portion of the formation sample and determining densities of the minerals; determining, using a second portion of the formation sample, material properties associated with said mineral densities; associating said material properties with the identified minerals using the mineral densities; and generating a log comprising the associations. Such embodiments may be supplemented in a variety of ways, including by adding any of the following concepts or steps, in any sequence and in any combination: identifying the minerals present in said first portion and determining the densities of the minerals comprises using energy dispersive spectrometry (EDS); determining said material properties comprises using computerized tomography (CT) on said second portion; said densities are relative densities; the material properties are selected from the group consisting of count information of each identified mineral in the formation sample and grain size distribution of each identified mineral in the formation sample; the first portion comprises a surface layer of the formation sample; the second portion is larger than the first portion; the first portion forms part of the second portion.

At least some of the embodiments disclosed herein are directed to a method that comprises, using energy dispersive spectrometry (EDS), identifying minerals present in a surface layer of a formation sample and determining densities associated with each of said minerals; generating a list of the identified minerals ordered according to their corresponding densities; using computerized tomography (CT) on a portion of the formation sample, identifying material properties associated with said mineral densities; generating a list of the material properties ordered according to their corresponding densities; comparing the densities in the ordered lists to determine relationships between the identified minerals and the identified material properties; and generating a log comprising the relationships. Such embodiments may be supplemented in a variety of ways, including by adding any of the following concepts or steps, in any sequence and in any combination: comparing said densities in the ordered lists to determine said relationships comprises locating matching densities in the ordered lists and associating the identified minerals and material properties corresponding to said matching densities; said portion is larger than the surface layer; the densities in the ordered lists are relative densities; identifying the material properties associated with the mineral densities comprises determining a number of minerals in said portion of the formation sample, determining mineral densities associated with each of the number of minerals, and determining material properties associated with each of the number of minerals; and using CT comprises using a cylindrical container comprising multiple partitions that hold the formation sample in place.

At least some of the embodiments disclosed herein are directed to a method that comprises obtaining a container having multiple partitions; positioning multiple formation samples between said partitions such that each formation sample contacts two or more partitions; using computerized tomography (CT), identifying material properties corresponding to the multiple formation samples and mineral densities corresponding to the multiple formation samples; matching the identified mineral densities to densities obtained from the multiple formation samples using energy dispersive spectroscopy (EDS); based on said matching, determining relationships between minerals in the formation samples and said material properties; and generating a log comprising the relationships. Such embodiments may be supplemented in a variety of ways, including by adding any of the following concepts or steps, in any sequence and in any combination: identifying the material properties and the mineral densities comprises performing CT on portions of the multiple formation samples that are larger than those upon which EDS is performed; the container comprises a low-density material; using CT comprises using a first scanning resolution and using EDS comprises using a second scanning resolution, wherein the first and second scanning resolutions vary by no more than 1 μm; identifying the material properties comprises one or more of identifying count information of each mineral in the formation samples and grain size distribution of each mineral in the formation samples; identifying the material properties and the mineral densities comprises determining a number of minerals in a portion of the formation sample, determining relative mineral densities associated with the number of minerals, and determining material properties associated with each of the number of minerals.

What is claimed is:

1. A method, comprising:
    using energy dispersive spectrometry (EDS), identifying minerals present in a surface layer of a formation sample and determining densities associated with each of said minerals;
    generating a list of the identified minerals ordered according to their corresponding densities;
    using computerized tomography (CT) on a portion of the formation sample, identifying material properties associated with said mineral densities;
    generating a list of the material properties ordered according to their corresponding densities;
    comparing the densities in the ordered lists to determine relationships between the identified minerals and the identified material properties;
    generating a log comprising the relationships;
    determining properties of a subsurface formation from which the formation sample is obtained from the generated log; and
    estimating an amount and location of hydrocarbon reserves in the subsurface formation from the determined properties of the subsurface formation.

2. The method of claim 1, wherein comparing said densities in the ordered lists to determine said relationships comprises locating matching densities in the ordered lists and associating the identified minerals and material properties corresponding to said matching densities.

3. The method of claim 1, wherein said portion is larger than the surface layer.

4. The method of claim 1, wherein the densities in the ordered lists are relative densities.

5. The method of claim 1, wherein identifying the material properties associated with the mineral densities comprises determining a number of minerals in said portion of the formation sample, determining mineral densities associated with each of the number of minerals, and determining material properties associated with each of the number of minerals.

6. The method of claim 1, wherein using CT comprises using a cylindrical container comprising multiple partitions that hold the formation sample in place.

7. The method of claim 1 wherein the properties of the subsurface formation are selected from the group consisting of rock permeability, types and amounts of mineral deposits, and grain size distribution.

8. A method, comprising:
obtaining a container having multiple partitions;
positioning multiple formation samples between said partitions such that each formation sample contacts two or more partitions;
using computerized tomography (CT), identifying material properties corresponding to the multiple formation samples and mineral densities corresponding to the multiple formation samples;
matching the identified mineral densities to densities obtained from the multiple formation samples using energy dispersive spectroscopy (EDS);
based on said matching, determining relationships between minerals in the formation samples and said material properties;
generating a log comprising the relationships;
determining properties of a subsurface formation from which the formation sample is obtained from the generated log; and
estimating an amount and location of hydrocarbon reserves in the subsurface formation from the determined properties of the subsurface formation.

9. The method of claim 8 wherein the properties of the subsurface formation are selected from the group consisting of rock permeability, types and amounts of mineral deposits, and grain size distribution.

10. The method of claim 8, wherein identifying the material properties and the mineral densities comprises performing CT on portions of the multiple formation samples that are larger than those upon which EDS is performed.

11. The method of claim 8, wherein the container comprises a low-density material.

12. The method of claim 8, wherein using CT comprises using a first scanning resolution and using EDS comprises using a second scanning resolution, wherein the first and second scanning resolutions vary by no more than 1 µm.

13. The method of claim 8, wherein identifying the material properties comprises one or more of: identifying count information of each mineral in the formation samples and grain size distribution of each mineral in the formation samples.

14. The method of claim 8, wherein identifying the material properties and the mineral densities comprises determining a number of minerals in a portion of the formation sample, determining relative mineral densities associated with the number of minerals, and determining material properties associated with each of the number of minerals.

15. The method of claim 1 further comprising determining effective strategies for extracting the hydrocarbon reserves from the determined properties of the subsurface formation.

16. The method of claim 8 further comprising determining effective strategies for extracting the hydrocarbon reserves from the determined properties of the subsurface formation.

* * * * *